United States Patent
Bullock

(10) Patent No.: US 11,660,222 B2
(45) Date of Patent: May 30, 2023

(54) METHODS AND SYSTEMS FOR TREATING HAND TREMORS

(71) Applicant: Robert Lee Bullock, Naperville, IL (US)

(72) Inventor: Robert Lee Bullock, Naperville, IL (US)

(*) Notice: Subject to any disclaimer, the term of this patent is extended or adjusted under 35 U.S.C. 154(b) by 0 days.

(21) Appl. No.: 17/544,513

(22) Filed: Dec. 7, 2021

(65) Prior Publication Data

US 2022/0175568 A1 Jun. 9, 2022

Related U.S. Application Data

(60) Provisional application No. 63/205,354, filed on Dec. 7, 2020.

(51) Int. Cl.
*A61F 5/01* (2006.01)

(52) U.S. Cl.
CPC ................... *A61F 5/0118* (2013.01)

(58) Field of Classification Search
CPC ........ A61F 5/0118; A61F 5/0104; A61F 5/01; A61F 5/013; A61F 5/05866; A61F 5/05875; A61F 5/10; A41D 19/01582; A41D 19/01588; A61H 1/0285; A61H 1/0288
USPC .......................................... 602/21; 601/5, 40
See application file for complete search history.

(56) References Cited

U.S. PATENT DOCUMENTS

| | | | |
|---|---|---|---|
| 4,689,449 A | 8/1987 | Rosen | |
| 6,553,574 B1 | 4/2003 | Hall et al. | |
| 6,730,049 B2 | 5/2004 | Kalvert | |
| 8,468,700 B2 | 6/2013 | Wilson | |
| 9,452,287 B2 | 9/2016 | Rosenbluth et al. | |
| 11,179,263 B1 | 11/2021 | Cofer et al. | |
| 2011/0030122 A1* | 2/2011 | Capurro | A61F 5/05875 2/163 |
| 2021/0106490 A1* | 4/2021 | Bhugra | A61F 2/72 |
| 2022/0000649 A1* | 1/2022 | Hepp | A61H 1/0288 |
| 2022/0008238 A1* | 1/2022 | Wang | A61F 5/0118 |

FOREIGN PATENT DOCUMENTS

| | | | | |
|---|---|---|---|---|
| EP | 3479809 A1 * | 5/2019 | ......... | A41D 19/0013 |
| WO | 2007044264 A2 | 4/2007 | | |
| WO | WO 2007044264 A2 | 4/2007 | | |
| WO | WO-2010117749 A2 * | 10/2010 | ............ | A61F 5/0118 |
| WO | 2016102958 A1 | 6/2016 | | |

(Continued)

OTHER PUBLICATIONS

Desroches et al., "Cyclic Properties of Superelastic Shape Memory Alloy Wires and Bars", Journal of Structural Engineering, Jan. 2004, pp. 38-46.

(Continued)

*Primary Examiner* — Victoria Hicks Fisher

(74) *Attorney, Agent, or Firm* — Cook Alex Ltd.

(57) ABSTRACT

A device for treating hand tremors and methods of using the device. In at least some embodiments, the device includes a glove covering and at least one Coulomb damping suspension assembly. In some embodiments, the Coulomb damping suspension assembly includes a flexible tube and a wire-tube assembly. In some embodiments, the wire-tube assembly includes a first length of a wire and a first tube.

14 Claims, 6 Drawing Sheets

(56) References Cited

FOREIGN PATENT DOCUMENTS

WO     WO 2016102958 A1     6/2016

OTHER PUBLICATIONS

Lora-Millan et al., "A Review on Wearable Technologies for Tremor Suppression", Frontiers in Neurology, vol. 12, Article 700600, Aug. 2021, pp. 1-17.

Pandey et al., "Editorial; Tremor Syndromes: Current Concepts and Future Perspectives", Frontiers in Neurology, vol. 12, Article 752463, Sep. 2021, pp. 1-2.

* cited by examiner

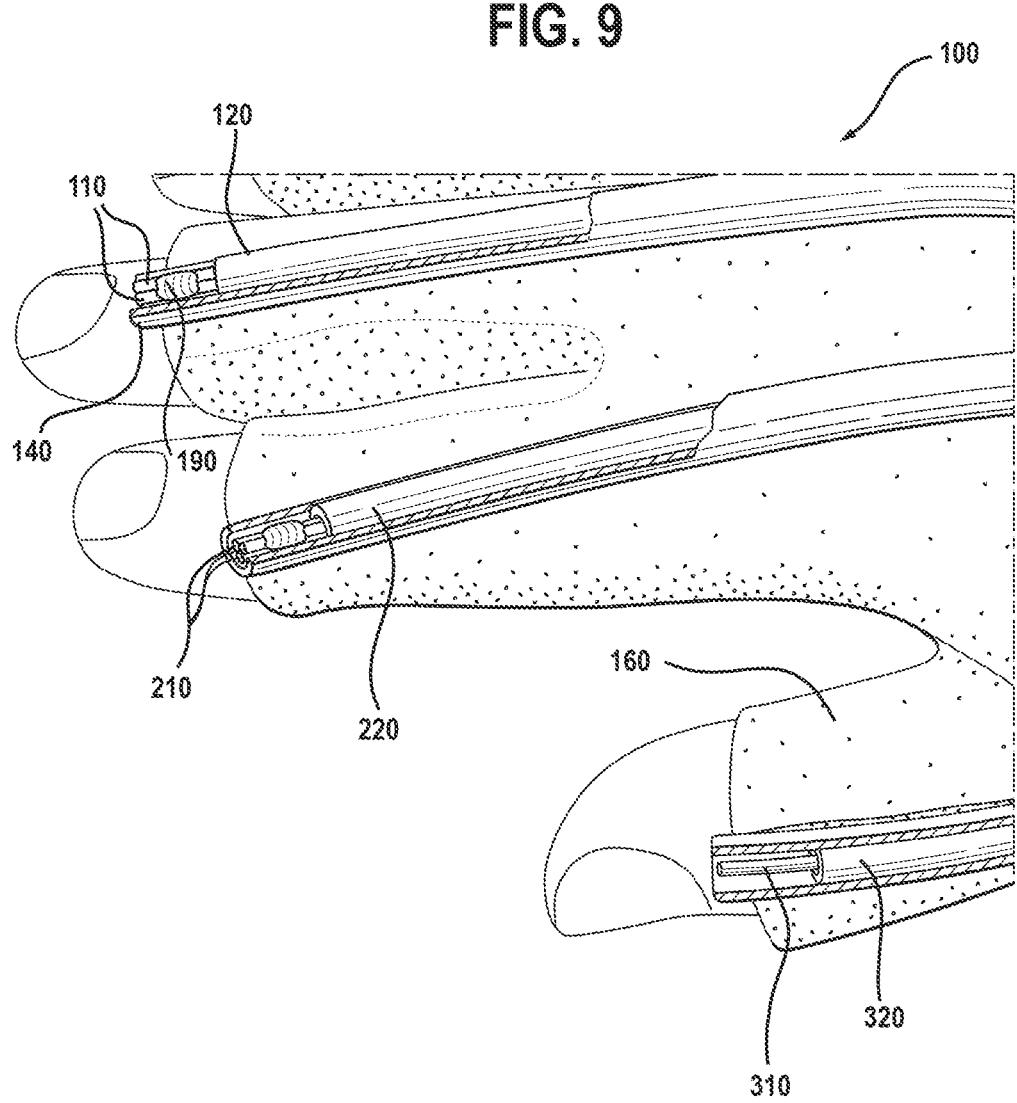

METHODS AND SYSTEMS FOR TREATING HAND TREMORS

CROSS-REFERENCE TO RELATED APPLICATIONS

This application is related to and claims priority benefits from U.S. Provisional Application Ser. No. 63/205,354 filed on Dec. 7, 2020.

The '354 application is hereby incorporated by reference herein in its entirety.

FIELD OF THE INVENTION

Over ten million people in the United States experience involuntary tremors, such as involuntary hand tremors (IHT) due to diseases or disorders, such as essential tremors or Parkinson's disease.

Hand tremors are involuntary, periodic, and mostly first order sinusoidal movements of the hand and/or fingers. In at least some instances, the kinematics of the tremors involve movements about the wrist, the hand-finger knuckle and/or the finger joints. Generally the primary movement about each bone joint is of a single degree of freedom but, in different two degree planes for each joint. In at least some instances the planes change angular relationship with each other during daily activities, especially the planes between the thumb and index finger during grasping an object.

Postural tremors occur when the hand joints are positioned against an external force, i.e., muscle loading. Generally, individuals suffering from involuntary hand tremors face difficulties in daily activities and can feel uncomfortable in social activities, such as dining. Hand tremors can give the impression to others of nervousness, strong feelings, and/or being physically unfit. People can have essential tremors their entire lives. Parkinson's disease on the other hand, is generally acquired later in life. However, hand tremors generally increase with age and negatively affect one's quality of life. People with essential tremors usually have postural tremors but not resting tremors. However, suffers of Parkinson's disease have both resting tremors and postural tremors.

Extensive research has been made regarding involuntary hand tremors with many mathematical models developed with various degrees of freedom. However models have not been developed about the three normal orthogonal axis and rotation about each axis for all six degrees of freedom possible for each finger with respect to the hand palm. For example, the kinematic motion of wriggling one's finger without moving the rest of the hand has up to 270 degrees of rotational change. It has been determined that the frequency of tremors generally runs from approximately 3 to 5 hertz to up to 10 hertz. The total displacement at the finger tips can range from a fraction of a centimeter (such as 0.4 cm) to several centimeters. In at least some instances, the velocity of the tremors is in the range of 200 meters per second (m/s) at midpoint. Accelerations of up to 10 m/s$^2$ have been detected.

The wrist, thumb, and each finger have their own unique kinematic and dynamic IHT responses. For example, the mass of a single human finger and hand can be estimated by assuming the hand has about the same density as water, 10 g/cm$^3$. For an average hand, the index finger has a mass of about 100 g. Using these measurements; displacement, velocity, acceleration, mass, and frequency of the index finger, and both the energy and power being pumped into the index finger by an IHT can be estimated. To control an IHT this energy and power can be controlled or dissipated. Ideally this is done with minimal, or at least reduced discomfort and/or hinderance to an individual's daily activities. Finally, each person's hand is different in size, strength, and IHT symptoms. In an ideal world this requires the control-dissipation device to be easily incrementally "tuned" for optimum IHT control for each individual hand and finger.

Currently, there are several approaches, with various known drawbacks, used to suppress IHT. Some methods involve the use of pharmaceuticals such as beta blockers, anti-seizure drugs, tranquilizers and/or Botox to slow the nerve misfires that cause IHT. However, current pharmaceuticals can have side effects, such as negatively affecting cardiac rhythms, and care must be taken when prescribing pharmaceuticals.

Other approaches for treating IHT involve neurosurgery and/or the use of neuro-implants. However, deep brain stimulation is invasive and involves expensive implants that only moderate IHT by modifying the nerve singles from the thalamus portion in the brain that causes tremors.

Still other approaches for treating IHT involve the use of mechanical devices consisting of linkage(s) that connect and integrate with sensor-control means. This assembly is then attached to the outside of the human body. To control IHT, the sensor detects the tremor movement activating the controller which in turn causes the exoskeleton linkages to resist or counter the IHT movements. These devices have reported 80% reduction in IHT. However, the devices are bulky, heavy, and uncomfortable to wear.

Still other approaches for treating IHT involve adding weight to the hands via a wearable device and/or using weighted utensils which adds mass to the hand and resists acceleration. While commonly marketed, this approach is not effective. While IHT causes vibration in various directions, the weighted devices and/or weighted utensils are biased towards the earth. Furthermore, vibration frequency is indirectly proportional to the square root of the value of mass. Unfortunately the amount of mass that can be added by these devices (while still making them useable) only reduces the tremor frequency around 3% to 9%.

Still other approaches for treating IHT involve using the concept of momentum. Momentum is directly proportional to the mathematical product of the object's mass and the object's velocity. In some embodiments, a spinning mass gyroscopic device has been developed for mounting on the back of the hand to control IHT. In other embodiments, a spring-mass system device (commonly referred to as a vibration absorber) has been developed for mounting on the wrist to control IHT. A main disadvantage of these devices is that they stabilize the hand as if it were ping pong paddle. There is not individual control for finger tremors. In addition, these types of devices are bulky and/or require a motor and power source. In regard to the vibration absorbers, it is possible for the devices to bottom out.

Still other approaches for treating IHT involve damping (restraining of vibratory motion by dissipation of energy). Current approaches using damping rely on viscous dampening and structural dampening. Viscous damping develops the restraining motion by a body passing through a fluid, compressible or incompressible. The resisting force is directly proportional to the velocity. Viscous damping devices are bulky, unidirectional and do not control for individual finger tremors.

Structural damping develops the restraining motion from the friction within the material itself and is proportional to the maximum stress due to vibratory motion. Structural damping devices cannot remove sufficient energy to control IHT. Furthermore, structural damping devices can crack and fail if the endurance stress of the material is exceeded too many times.

A third type of dampening is known as Coulomb damping. Coulomb damping develops the restraining motion from the sliding of two dry surfaces against each other and is directly proportional to the normal force between them. Coulomb damping has been used to dampen suspension of larger vehicles, such as railroad freight cars for decades. One benefit of Coulomb damping is that it adds little bulk or weight to a system. For example, in some embodiments, a Coulomb dampening system would only add roughly 30 grains per hand. Additionally, Coulomb damping systems have long life expectancies. In fatigue design of dynamic structures, ten million maximum loading cycles is considered infinite life. For a Coulomb damping system at five hertz frequency at maximum displacement a minimum life expectancy of 500 hours would be expected. If failure occurs the system would revert to a failsafe condition. What are needed are devices for treating IHT that utilizes Coulomb damping systems.

SUMMARY OF THE INVENTION

In some embodiments, a device for stabilizing a hand can include a glove covering and a first Coulomb damping suspension assembly. In some embodiments, the first Coulomb damping suspension assembly can include a first flexible tube and a first wire-tube assembly. In some embodiments, the first wire-tube assembly includes a first length of a wire and a first tube.

In some embodiments, the first wire-tube assembly further includes a first plurality of wires.

In some embodiments, the length of the first tube is longer than the length of said first plurality of wires.

In some embodiments, the first tube is a polyolefin heat shrink tube.

In some embodiments, the wire has a diameter of 0.5 mm. In some embodiments, the wire is made of a shape-memory alloy. In some embodiments, the wire is made of nitinol.

In some embodiments, the device includes a second Coulomb damping suspension assembly, a third Coulomb damping suspension assembly, a fourth Coulomb damping suspension assembly, and/or a fifth Coulomb damping suspension assembly.

In some embodiments, the second Coulomb damping suspension assembly includes a second flexible tube and a second wire-tube assembly.

In some embodiments, the second wire-tube assembly includes a second plurality of wires and a second tube.

In some embodiments, the third Coulomb damping suspension assembly includes a third flexible tube and a third wire-tube assembly.

In some embodiments, the third wire-tube assembly includes a third plurality of wires and a third tube.

In some embodiments, the first Coulomb damping suspension assembly is configured to extend on the dorsal side of a user's hand from the radius-ulna side of the carpal over the carpal, metacarpal, and metacarpophalangeal joint just past the proximal interphalangeal joint of a first phalange.

In some embodiments, the first plurality of wires is made up of a number of wires that is different than a second number of wires that makes up the second plurality of wires. In some embodiments, the first plurality of wires is made up of a first material and the second plurality of wires is made up of a second material. In some embodiments, the first plurality of wires has a first diameter and the second plurality of wires has a second diameter.

In some embodiments, the first wire-tube assembly is attached at one end to the first flexible tube.

In some embodiments, the glove covering is made, at least in part of, of a latex, a nylon and/or a polyester.

In some embodiments, the device weighs less than 34 grains.

In some embodiments, the device reduces tremors by at least 90%.

A method of stabilizing a hand by using a hand tremor coulomb stabilizer is disclosed below.

BRIEF DESCRIPTION OF THE DRAWINGS

FIG. 9 is a partial cross sectional perspective view of a device for controlling hand tremors.

DETAILED DESCRIPTION OF PREFERRED EMBODIMENT(S)

Figure 1:
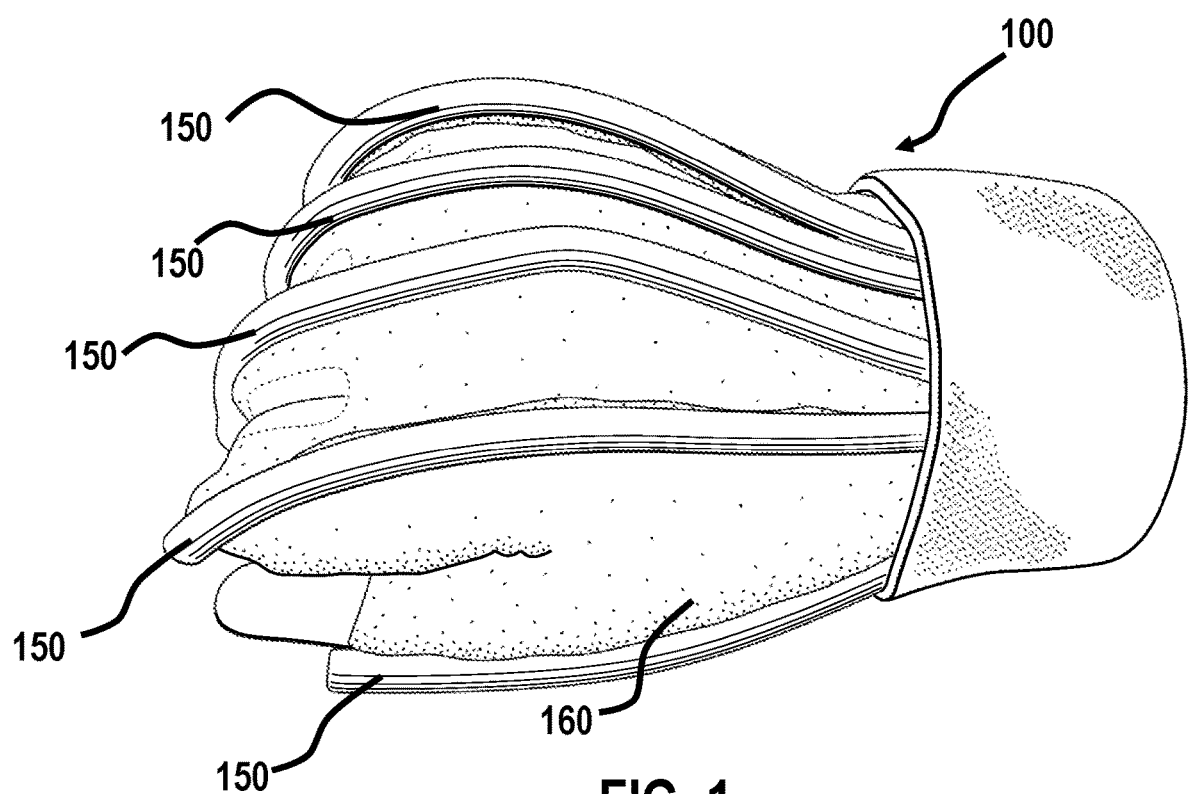
FIG. 1 is a perspective view of a device for controlling hand tremors being used with a user's hand in the closed position.
Figure 2:
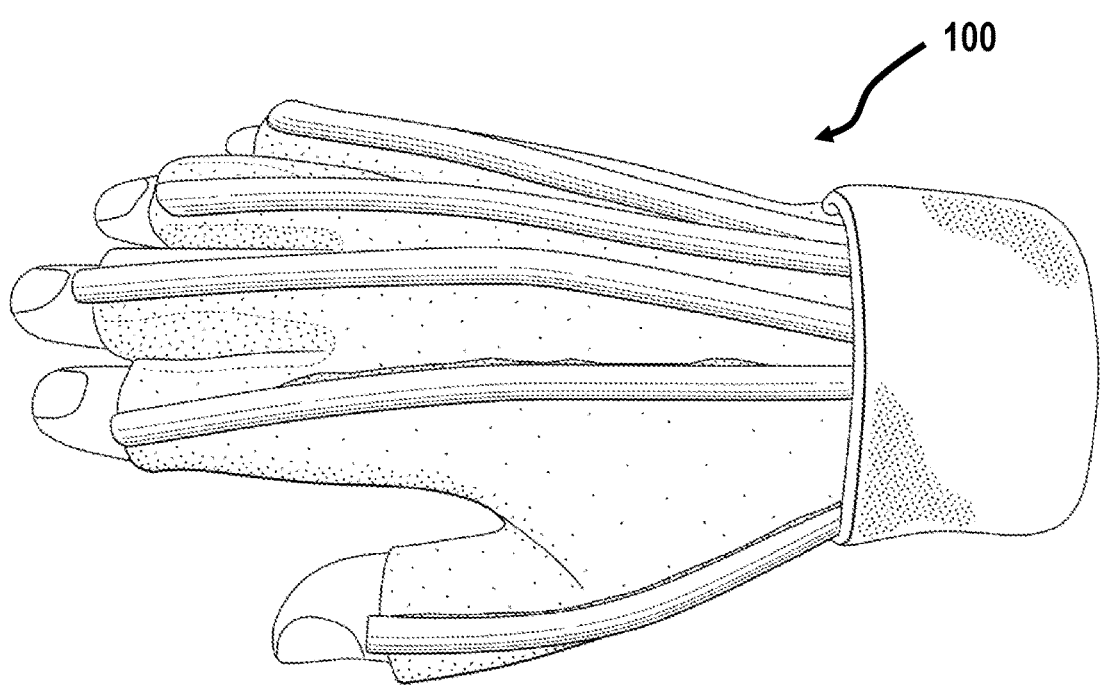
FIG. 2 is a perspective view of a device for controlling hand tremors being used with a user's hand in the open position.
Figure 3:
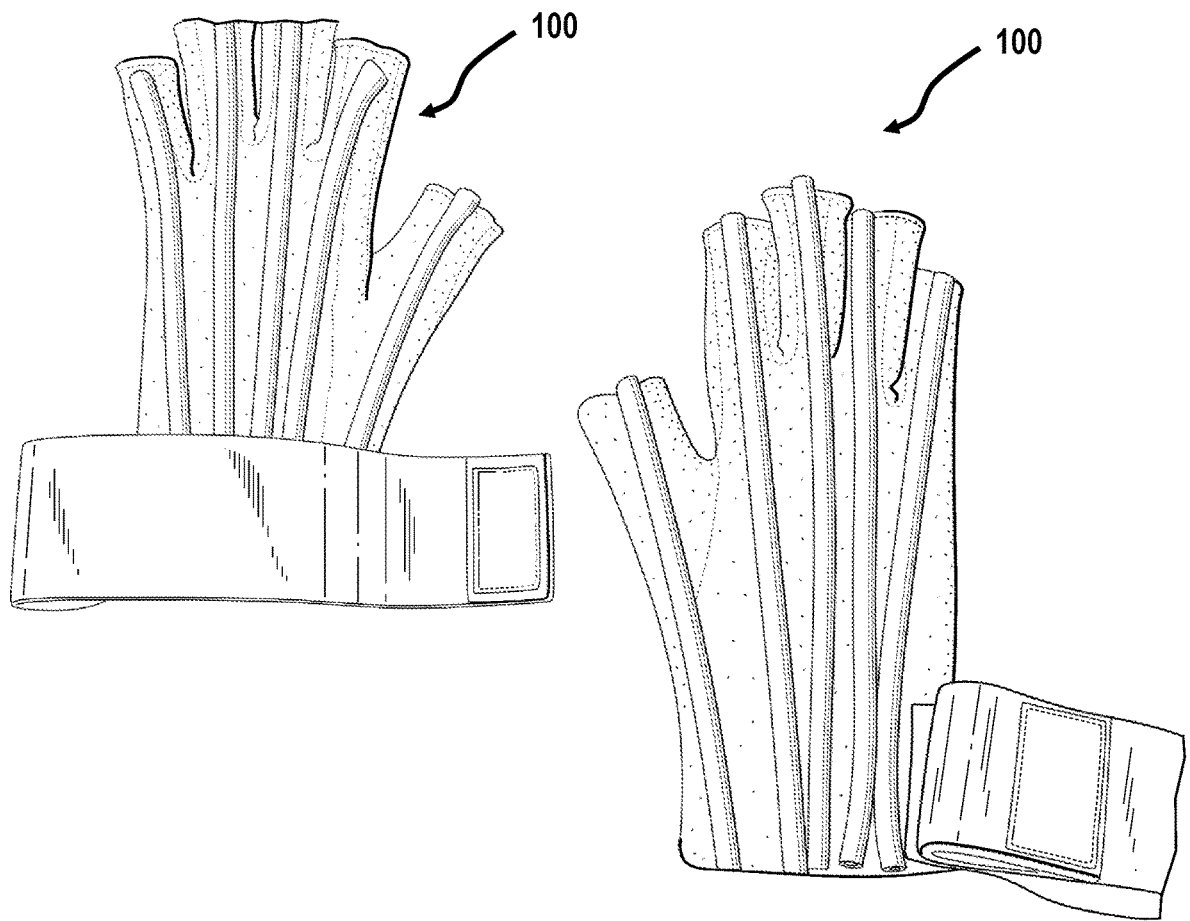
FIG. 3 a perspective view of a pair of devices for controlling hand tremors.
Figure 4:
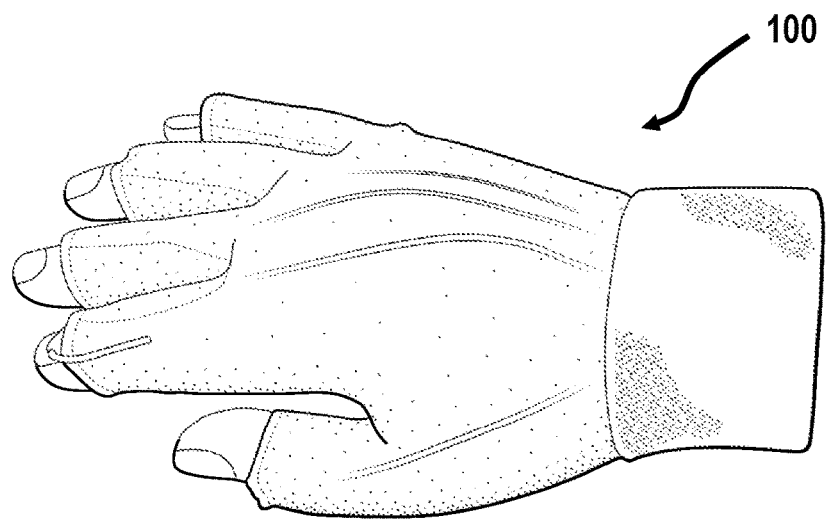
FIG. 4 is a semitransparent view of another embodiment of a device for controlling hand tremors being used with a user's hand in the open position.
Figure 5:
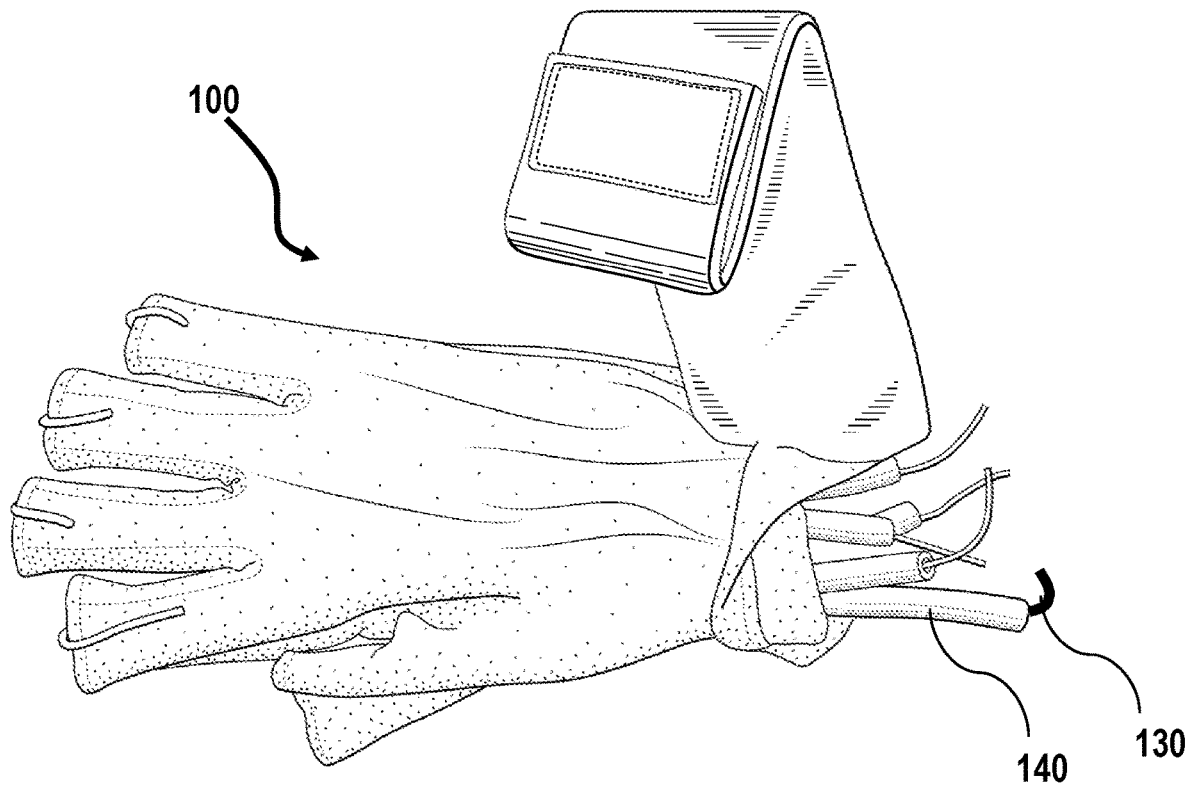
FIG. 5 is a perspective view of another embodiment of a device for controlling hand tremors.
Figure 6:
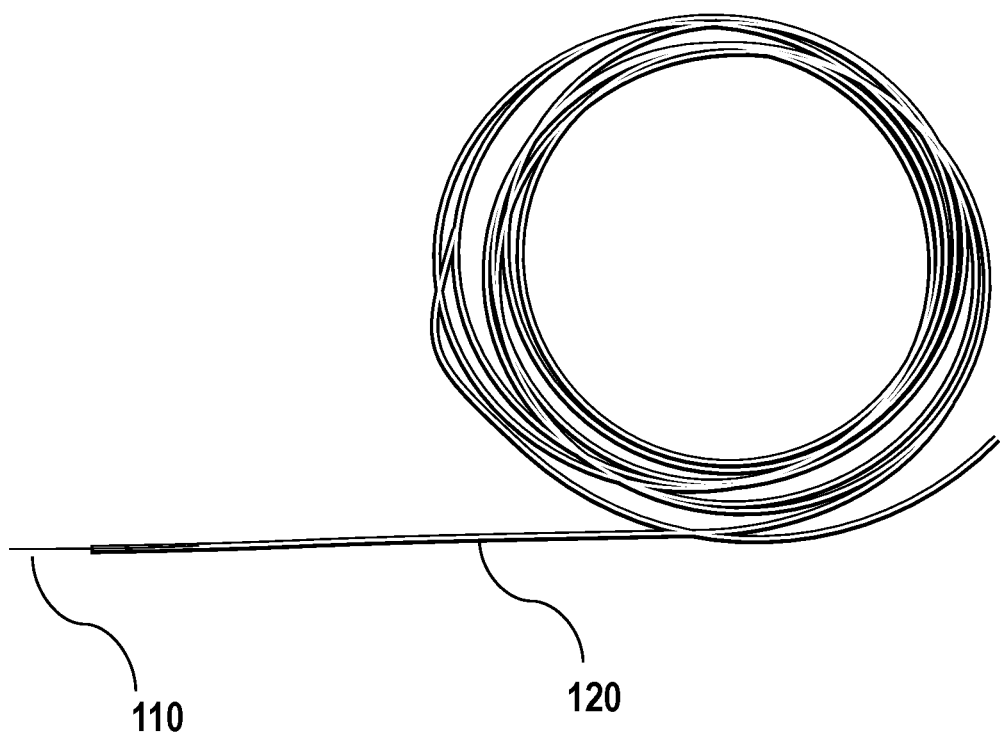
FIG. 6 is a top view of a wire being placed into a tube to form a wire-tube assembly.
Figure 7:
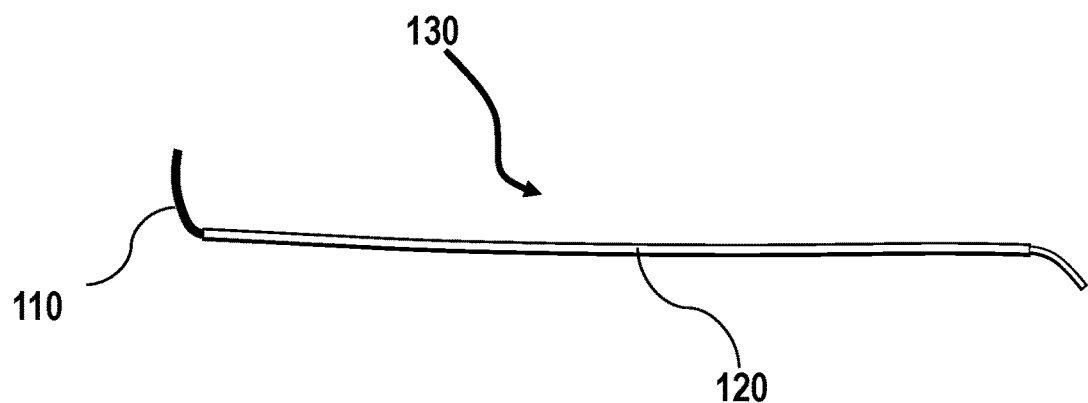
FIG. 7 is a top view of a wire-tube assembly.
Figure 8:
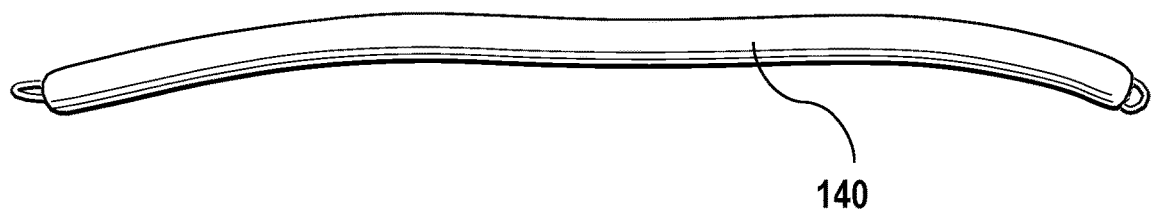
FIG. 8 is a top view of a flexible tube.

FIG. 1 is a perspective view of device 100 for controlling hand tremors. In some embodiments, device 100 is an IHT stabilizing device. In some embodiments, device 100 is a hand tremor coulomb stabilizer. In some embodiments, a length of wire 110 is inserted into a tube 120 to form wire-tube assembly 130. In some embodiments, multiple lengths of wire 110 are inserted into a tube 120 to form wire-tube assembly 130. In some embodiments, at least one end of the length of wires 110 are soldered and/or bonded together. In some embodiments, this keeps the wires aligned in the longitudinal direction.

In some embodiments, at least one end of the length of wires 110 are inserted into tube 120 such that the ends of the wires 110 are covered to prevent skin damage.

In some embodiments, tube 120 is a polyolefin heat shrink tube. In some of these embodiments, tube 120 is heated to a temperature of about 120° C. causing tube 120 to shrink and tightly hold wire(s) 110 together in the radial direction in wire-tube assembly 130. In some of these embodiments, tube 120 is longer than wires 110 (for example by at least 25 mm at each end). In some embodiments, the ends of tube 120 are folded back and bonded to prevent longitudinal creep or slippage of the wire(s) 110 during use.

In some embodiments, wire 110 has a diameter of 0.5 mm. In some embodiments, wire 110 has a diameter with a range between and inclusive of 0.2 mm to 1.0 mm. In some embodiments, wire 110 has a diameter with a range between and inclusive of 1.5 mm to 3.0 mm. In some embodiments, wire 110 is made of a metal. In some embodiments, wire 110 is made, at least in part, of a shape-memory alloy. In some embodiments, wire 110 is made, at least in part, of a material with superelasticity/pseudoelasticity properties. In some embodiments, wire 110 is made, at least in part, of nitinol. In some embodiments, other metals can be used such as steel.

In some embodiments, nitinol is used for its shape recovering properties at room temperature. Nitinol can accommodate the nonsymmetrical muscle strength of the hand during the flection of the hand and/or fingers. Nitinol also exhibits structural damping. However, research has determined this damping is of low value (less than 7% of equivalent viscous damping or 3% of critical damping limit). Therefore, additional damping from another source is necessary to dissipate unwanted energy generated by IHT.

In some embodiments, device 100 includes a plurality of wire-tube assemblies 130. In some embodiments, device 100 includes two wire-tube assemblies 130. In some embodiments, device 100 includes three wire-tube assemblies 130. In some embodiments, device 100 includes four wire-tube assemblies 130. In some embodiments, device 100 includes five wire-tube assemblies 130.

In some embodiments, the length of wires 110 should have a length such that each extends on the dorsal side of a user's hand from the radius-ulna side of the carpal over the carpal, metacarpal, and metacarpophalangeal joint just past the proximal interphalangeal joint of each phalange.

In some embodiments, wires 110 do not extend over the distal interphalangeal joint. In at least some embodiments, this allows for a user to retain touch sensitivity at the fingertip.

In some embodiments, a first phalange can utilize a first wire-tube assembly 130 with a first number of wires 110 and a second phalange can utilize a second wire-tube assembly 130 with a second number of wires 110. In some embodiments, this is done to account for different muscular strengths of the first phalange and the second phalange. In some embodiments, a first phalange can utilize a first wire-tube assembly 130 with a first number of wires 110, a second phalange can utilize a second wire-tube assembly 130 with a second number of wires 110, a third phalange can utilize a third wire-tube assembly 130 with a third number of wires 110, a fourth phalange can utilize a fourth wire-tube assembly 130 with a fourth number of wires 110, and/or a fifth phalange can utilize a fifth wire-tube assembly 130 with a fifth number of wires 110. In some embodiments, this is done to account for different muscular strengths of the various phalanges.

In some embodiments, a first phalange can utilize a first wire-tube assembly 130 with wires 110 made of a first material and a second phalange can utilize a second wire-tube assembly 130 with wires 110 made of a second material. In some embodiments, a first phalange can utilize a first wire-tube assembly 130 with wires 110 made of a first material, a second phalange can utilize a second wire-tube assembly 130 with wires 110 made of a second material, a third phalange can utilize a third wire-tube assembly 130 with wires 110 made of a third material, a fourth phalange can utilize a fourth wire-tube assembly 130 with wires 110 made of a fourth material, and/or a fifth phalange can utilize a fifth wire-tube assembly 130 with wires 110 made of a fifth material. In some embodiments, this done to account for different muscular strengths of the various phalanges.

In some embodiments, a first phalange can utilize a first wire-tube assembly 130 with wires 110 with a first diameter and a second phalange can utilize a second wire-tube assembly 130 with wires 110 with a second diameter. In some embodiments, a first phalange can utilize a first wire-tube assembly 130 with wires 110 with a first diameter, a second phalange can utilize a second wire-tube assembly 130 with wires 110 with a second diameter, a third phalange can utilize a third wire-tube assembly 130 with wires 110 with a third diameter, a fourth phalange can utilize a fourth wire-tube assembly 130 with wires 110 with a fourth diameter, and/or a fifth phalange can utilize a fifth wire-tube assembly 130 with wires 110 with a fifth diameter. In some embodiments, this is done to account for different muscular strengths of the various phalanges.

In some embodiments, the number of wires used, diameter of the wires, and/or material of the wires can vary among the various wire tube assemblies.

Using these methods gives the ability to fine tune device 100 to each user's specification. For example, doubling the number of wires increases the stiffness by a factor of two while doubling the diameter of the wire increases the stiffness by a factor of four. In some embodiments, wire-tube assemblies 130 are relatively easy to switch out, such that device 100 can be easily adjusted based on a user's changing condition.

In at least some embodiments, wire-tube assembly 130 is inserted into flexible tube 140. In some embodiments, flexible tube 140 has an inside diameter of roughly twice the outside diameter of wire-tube assembly 130. In some embodiments, flexible tube 140 has an inside diameter between and inclusive of 1.5 mm to 5 mm. In some embodiments, flexible tube 140 is made of a polymer. In some embodiments, flexible tube 140 is made of a natural rubber.

In at least some embodiments, flexible tube 140 has approximately the same length of that of wire 110. In some embodiments, one end of wire-tube assembly 130 is securely attached to one end of flexible tubing 140. In some embodiments, means for creating the attachment, include but are not limited to, using a flexible bonding agent, adhesive and/or mechanical means such as sewing materials or fabric clips.

The assembly of wire-tube assembly 130 and flexible tube 140 makes up Coulomb damping suspension assembly 150. In at least some embodiments, Coulomb damping suspension assembly 150 controls the undesirable energy and vibrational osculation of IHT by the sliding of wire-tube assembly 130 against the inside surface of flexible tube 140.

In some embodiments, device 100 includes a plurality of Coulomb damping suspension assemblies 150. In some embodiments, device 100 includes two Coulomb damping suspension assemblies 150. In some embodiments, device 100 includes three Coulomb damping suspension assemblies 150. In some embodiments, device 100 includes four Coulomb damping suspension assemblies 150. In some embodiments, device 100 includes five Coulomb damping suspension assemblies 150.

In at least some embodiments, Coulomb damping suspension assembly 150 is held firmly against the dorsal side of a user's hand. In at least some embodiments, this is accomplished with glove covering 160. In at least some embodiments, glove covering 160 is sufficiently flexible to allow the flexible tubing outer surface of Coulomb damping suspension assembly 150 to stretch and relax. In at least some embodiments, there is no relative motion between the tubing and skin during normal activities.

In some embodiments, glove covering 160 utilizes hook-and-loop straps. In some embodiments, glove covering 160 utilizes snaps, buttons, and/or magnetic fastening mechanisms. In some embodiments, at least part of glove covering 160 is made of wholly, or in part, materials such as, but not limited to, latex, Spandex®, nylon, polyester and/or other similar materials with elastic properties.

In at least some embodiments, when device 100 is constrained against the dorsal side of the hand along the path from over the wrist and along the length of the series of hand bones for each phalange its length extends when the hand bends inward and contracts when the hand is straightened. The muscles of the hand are non-symmetrical in that the muscles are much more powerful when bending the hand inward than opening up the hand. Angular displacement of the human fingertip is quite large (up to three-hundred-and-sixty degrees from a flat hand to a closed fist). In at least some embodiments, device 100 dissipates the energy from the tremors while accommodating the gross movement of the hand with minimal, or at least little, hindrance.

Hand tremors are involuntary, periodic, and mostly a first order sinusoidal movements of the hand and/or fingers. In at least some embodiments, excessive forced cyclic movement of a mass is controlled by a suspension system comprised of springs and dampers. In at least some embodiments of device 100, the properly tuned spring rate for each finger is provided primarily by bending of wire(s) 110. In at least some embodiments of device 100, the damping is produced by the Coulomb damping force generated between the outer surface of wire-tube assembly 130 and the inside surface of flexible tube 140. In at least some embodiments for hand and/or finger movements, flexible tube 140 is constrained to follow the dorsal surface of the hand as it extends and contracts while the wire-tube assembly 130 within does not change length. The relative motion between the wire-tube assembly 130 and flexible tube 140 generates the Coulomb damping.

In at least some embodiments, device 100 reduces the tremor in a hand and at least one finger by at least 90%. In at least some embodiments, device 100 reduces the tremor in a hand and at least one finger by at least 80%. In at least some embodiments, device 100 reduces the tremor in a hand and at least one finger by at least 70%.

In at least some embodiments, device 100 reduces the tremor in a hand and each finger by at least 90%. In at least some embodiments, device 100 reduces the tremor in a hand and each finger by at least 80%. In at least some embodiments, device 100 reduces the tremor in a hand and each finger by at least 70%.

In at least some embodiments, device 100 increases the hand weight of user by less than 35 grains per hand. In some embodiments, device 100 weighs less than 34 grains.

In at least some embodiments, device 100 is noninvasive, not unwieldy, or bulky. In at least some embodiments, device 100 is durable and requires minimal maintenance. In at least some embodiments, device 100 does not require electrical power. In at least some embodiments, device 100 can be put on by a user with minimal, if any, assistance. In at least some embodiments, device 100 cost less to produce than current treatment options. In at least some embodiments, device can also incorporate current systems such as spring-based vibration absorbers and/or gyroscopic devices.

In some embodiments, such as the one shown in FIG. 9, a first phalange can utilize a first wire-tube assembly with a first plurality of wires 110 in a first tube 120, a second phalange can utilize a second wire-tube assembly with a second plurality of wires 210 in a second tube 220 and/or a third phalange can utilize a third wire-tube assembly with a third plurality of wires 310 in a third tube 320. In some embodiments, the first plurality of wires is made up of a number of wires that is different than a second number of wires that makes up the second plurality of wires. In the embodiment illustrated in FIG. 9, the first plurality of wires is made up of two wires, the second plurality of wires is made up of three wires, and the third plurality of wires is made up of one wire.

In some embodiments, the first plurality of wires has a first diameter and the second plurality of wires has a second diameter. This can be due to the individual wires having different thicknesses in each plurality and/or due to the plurality of wires having differing number of wires in the pluralities. In the embodiment illustrated in FIG. 9, the first plurality of wires is made up of two wires with a first thickness and the second plurality of wires is made up of three wires with a second thickness, such that the diameter of said first plurality is different than the diameter of the second plurality.

In some embodiments, the first plurality of wires are soldered together such as shown in FIG. 9 by solder joint 190.

While particular elements, embodiments and applications of the present invention have been shown and described, it will be understood, that the invention is not limited thereto since modifications can be made without departing from the scope of the present disclosure, particularly in light of the foregoing teachings.

What is claimed is:

1. A device for stabilizing a hand comprising:
   (A) a glove covering;
   (B) a first Coulomb damping suspension assembly comprising:
      (I) a first flexible tube; and
      (II) a first wire-tube assembly comprising;
         (a) a first plurality of wires with a first length of a wire; and
         (b) a first tube;
   (C) a second Coulomb damping suspension assembly comprising:
      (I) a second flexible tube; and
      (II) a second wire-tube assembly comprising:
         (a) a second plurality of wires; and
         (b) a second tube,
   wherein said first plurality of wires is made up of a number of wires that is different than a second number of wires that makes up said second plurality of wires.

2. The device for stabilizing said hand of claim 1 wherein said first plurality of wires are soldered together.

3. The device for stabilizing said hand of claim 1 wherein said first tube is a polyolefin heat shrink tube.

4. The device for stabilizing said hand of claim 1 wherein said first length of said wire has a diameter of 0.5 mm.

5. The device for stabilizing said hand of claim 1 wherein said wire is made of a shape-memory alloy.

6. The device for stabilizing said hand of claim 1 wherein said wire is made of nitinol.

7. The device for stabilizing said hand of claim 1 further comprising
   (D) a third Coulomb damping suspension assembly comprising:
      (I) a third flexible tube; and
      (II) a third wire-tube assembly comprising;
         (a) a third plurality of wires; and
         (b) a third tube.

8. The device for stabilizing said hand of claim 1 wherein said first Coulomb damping suspension assembly is configured to extend on the dorsal side of a user's hand from the radius-ulna side of the carpal over the carpal, metacarpal, and metacarpophalangeal joint just past the proximal interphalangeal joint of a first phalange.

9. The device for stabilizing said hand of claim 1, wherein said first plurality of wires is made up a first material and said second plurality of wires is made up of a second material.

10. The device for stabilizing said hand of claim 1, wherein said first plurality of wires have a first diameter and said second plurality of wires have a second diameter.

11. The device for stabilizing said hand of claim 1 wherein said first wire-tube assembly is attached at one end to said first flexible tube.

12. The device for stabilizing said hand of claim 1 wherein said glove covering is made, at least in part of, of a latex, a nylon and/or a polyester.

13. The device for stabilizing said hand of claim 1 wherein said device weighs less than 34 grams.

14. The device for stabilizing said hand of claim 1 wherein said device is capable of reducing tremors by at least 90%.

* * * * *